United States Patent [19]
Baum

[11] Patent Number: 5,804,180
[45] Date of Patent: Sep. 8, 1998

[54] *BACILLUS THURINGIENSIS* STRAINS SHOWING IMPROVED PRODUCTION OF CERTAIN LEPIDOPTERAN-TOXIC CRYSTAL PROTEINS

[75] Inventor: James Baum, Doylestown, Pa.

[73] Assignee: Ecogen, Inc., Langhorne, Pa.

[21] Appl. No.: 682,325

[22] Filed: Jul. 17, 1996

[51] Int. Cl.$^6$ ............... A01N 63/00; C12N 1/20; C12N 1/21; C12N 15/32
[52] U.S. Cl. ............... 424/93.461; 435/252.31; 435/252.5; 435/172.3
[58] Field of Search ............ 435/252.31, 252.5, 435/69.1, 713; 530/350; 424/93.461; 514/2, 12; 536/23.71

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,990,332 | 2/1991 | Payne et al. | 424/93.461 |
| 4,996,156 | 2/1991 | Zaehner | 435/252.5 |
| 5,006,336 | 4/1991 | Payne | 435/93.461 |
| 5,441,884 | 8/1995 | Baum | 435/252.31 |

FOREIGN PATENT DOCUMENTS

| | | |
|---|---|---|
| 0 099 301 | 7/1983 | European Pat. Off. . |
| 0 228 228 | 12/1986 | European Pat. Off. . |
| WO 91/07481 | 5/1991 | WIPO . |
| WO 92/14826 | 9/1992 | WIPO . |
| WO 94/25611 | 11/1994 | WIPO . |
| WO 94/28724 | 12/1994 | WIPO . |

OTHER PUBLICATIONS

Baum, J.A., TnpI Recombinase: Identification of Sites within Tn5401 Required for TmpI Binding and Site-Specific Recombination *J. Bacteriol.* 1995 177:4036–4042.

Brussock et al. Use of Sodium Dodecyl Sulfate–Polyacrylamide Gel Electrophoresis to Quantify *Bacillus thuringiensis* δ–Endotoxins *Analytical Chemistry of Bacillus thuringiensis.* (L.A.Hickle and W.L.Fitch, eds.) The American Chemical Society Ch. 9 1990 78–87.

Chak et al. Expression of the Crystal Protein Gene Under the Control of the α–Amylase Promoter in Bacillus Thuringiensis Strains *Appl. Environ. Microbiol.* 1994 60:2304–2310.

Donovan et al. Characterization of Two Genes Encoding Bacillus thuringiensis Insecticidal Crystal Proteins Toxic to Coleoptera Species *Appl. Environ. Microbiol.* 1992 58:3921–3927.

Donovan et al. Amino Acid Sequence and Entomocida Activity of the P2 Crystal Protein *J. Biol. Chem.* 1988 263:561–567.

DuBois et al. Synergism Between CryIA Insecticidal Proteins and Spores of Bacillus thuringiensis, Other Bacterial Spores, and Vegetative Cells Against Lymantria Dispar *Biological Control* 1995 24:1741–1747.

Gawron–Burke et al. Genetic Manipulation of Bacillus thuringiensis Insecticidal Crystal Protein Genes in Bacteria *Genetic Engineering* 1991 13:237–263.

Schnepf et al. Cloning and expression of the Bacillus thuringiensis crystal protein gene in *Escherichia coli Proc. Natl. Acad. Sci. USA* 1981 78:2893–2897.

Gonzalez Jr. et al. Transfer of Bacillus thuringiensis plasmids coding for δ–endotoxin among strains fo B. Thuringiensis and B. Cereus *Proc. Natl. Acad. Sci USA* 1982 79:6951–6955.

Höfte et al. Insecticidal Crystal Proteins of Bacillus thuringiensis *Microbiol. Rev.* 1989 53:242–255.

Mettus et al. Expression of Bacillus thuringiensis δ–Endotoxin Genes during Vegetative Growth *Appl. Environ. Microbiol.* 1990 56:1128–1134.

Moar et al. development of Bacillus thuringiensis CryIC Resistance by Spodoptera exigua *Appl. Environ. Microbiol.* 1995 61:2086–2092.

Tang et al. Toxicity of Bacillus thuringiensis Spore and Crystal Protein to Resistant Diamondback Moth *Appl. Environ. Microbiol.* 1996 62:564–569.

*Primary Examiner*—Robert A. Wax
*Assistant Examiner*—Gabriele E. Bugaisky
*Attorney, Agent, or Firm*—Woodcock Washburn Kurtz Mackiewicz & Norris LLP

[57] ABSTRACT

The present invention is directed to *Bacillus thuringiensis* isolates active against lepidopteran pests, and certain lepidopteran-toxic crystal proteins produced by the *Bacillus thuringiensis* isolates.

6 Claims, 4 Drawing Sheets

ND-1800

BACILLUS THURINGIENSIS STRAINS SHOWING IMPROVED PRODUCTION OF CERTAIN LEPIDOPTERAN-TOXIC CRYSTAL PROTEINS

FIELD OF THE INVENTION

The present invention relates to variant *Bacillus thuringiensis*, (*B. thuringiensis*, or *B.t.*) strains that produce increased amounts of certain lepidopteran-active insecticidal crystal proteins and exhibit normal sporulation. The invention also relates to derivative strains that retain the ability to produce increased amounts of certain lepidopteran-toxic crystal proteins and normal sporulation.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kurstaki HD-1 produces a crystal inclusion consisting of biotoxins called delta endotoxins or insecticidal crystal proteins (Cry) which are toxic to the larvae of a number of lepidopteran insects. The cloning, sequencing, and expression of an HD1 *B.t.* crystal protein gene in *Escherichia coli* has been described in the published literature (Schnepf, H. E. and Whitely, H. R., *Proc. Natl. Acad. Sci. USA* 1981, 78:2893–2897; Schnepf et al.). U.S. Pat. Nos. 4,448,885 and 4,467,036 disclose the expression of *B.t.* crystal protein in *E. coli*.

*Bacillus thuringiensis* is a gram-positive bacterium that typically produces proteinaceous crystalline inclusions during sporulation. These *B.t.* crystal proteins or delta endotoxins are a large collection of insecticidal crystal proteins which are highly toxic to specific insects and are an active ingredient in commercial *B.t.*-based biological insecticides. Crystal proteins from various *B.t.* strain isolates have been identified as having insecticidal activity against insect larvae from the insect orders Lepidoptera (caterpillars), Coleoptera (beetles), Diptera (mosquitoes, flies), and Homoptera (aphids). The insecticidal crystal proteins (ICPs) of *B. thuringiensis* were originally classified as CryI, CryII, CryIII, and CryIV proteins based on their insecticidal activities (Hofte H. and H. R. Whiteley, *Microbiol. Rev.* 1989, 53:242–255). More highly related proteins within each family are then assigned divisional letters such as CryIA, CryIB, CryIC, etc. Even more closely related proteins within each division are given names such as CryIC1, CryIC2, etc. (Hofte & Whitely, *Microbiol. Rev.* 1989, 53:242–255).

CryI proteins, which encompass crystal proteins of approximately 130–140 kilodaltons (kDa) in molecular mass, display lepidopteran toxicity. CryII proteins are approximately 71 kDa in mass and may display both lepidopteran and dipteran toxicity. CryIII proteins are approximately 73–74 kDa in mass and display coleopteran toxicity. The CryIV proteins represent a diverse group of proteins that exhibit dipteran toxicity. For the purpose of this disclosure, the original Hofte and Whiteley nomenclature will be used.

Commercial *B.t.* bioinsecticide products currently being marketed for lepidopteran insect control are based on either naturally occurring ("native") strains or transconjugant strains. Transconjugant strains are created by transferring a crystal protein-encoding plasmid from a donor strain to a recipient strain via a conjugation-like process, resulting in a new *B.t.* strain. Plasmids may also be transferred from one strain to another by phage transduction. Native and transconjugant strains are fermented in a broth medium, the spores and crystals harvested, either by spray-drying, centrifugation, or otherwise, and subsequently formulated for spray or other application.

The insecticidal activity of these *B.t.* bioinsecticides, like that of all *B.t.*-based commercial products, is believed to result from insect larvae feeding on the crystal protein, typically in sprayed-on deposits of the bioinsecticide on leaves or other plant surfaces. General details of the mode of action of the insecticidal crystal proteins (ICPs) are apparent. The ICPs contained within the proteinaceous crystals are released into the insect midgut after ingestion and solubilization of the crystals at that location. In many instances, the proteins are processed by midgut proteases to a fully active state. The activated toxins bind to the brush border membranes (BBMs) of the insect midgut epithelium, a step that frequently requires the presence of fortuitous "receptor" proteins. This binding is followed by an apparent intercalation event in which the active toxin moiety, or a portion of it, contributes to the formation of ion channels as well as aggregates to form larger pores within the BBM, leading to osmotic imbalance, cellular swelling and lysis. Intoxicated insect larvae stop feeding within minutes and eventually die.

For many lepidopteran insect pests, such as the beet armyworm (*Spodoptera exigua*), the *B.t.* spores present in the bioinsecticide formulation also contribute substantially to toxicity. The synergistic effect of spores has been reported for a number of important lepidopteran insect pests, including *S. exigua* (Moar, W. J., et al., *Appl. Environ. Microbiol.* 1995, 61:2086–2092), *Lymantria dispar* (DuBois, N. and D. H. Dean, *Biological Control* 1995, 24:1741–1747), and *Plutella xylostella* (Tang, J. D., et al., *Appl. Environ. Microbiol.* 1996, 62:564–569). This spore effect on the insecticidal activity of *B.t.* may be due to septicemia: the ability of the spore to germinate within the insect midgut, to penetrate the disrupted midgut epithelium, and to enter and proliferate within the hoemcoel. For many lepidopteran insect pests, it is therefore desirable that the *B.t.* bioinsecticide formulation contain a mixture of spores and crystals to achieve maximal efficacy.

The amount of crystal protein produced in fermentation should be maximized as much as possible in order to provide for its economic and efficient utilization in the field. Increased concentration of crystal protein in the formulated bioinsecticide promotes use of reduced amounts of bioinsecticide per unit area of treated crop, without reducing the actual amount of crystal protein applied per unit area, thereby allowing for more cost-effective use of the bioinsecticide product. Alternatively, increased fermentation yields of crystal protein, resulting in more concentrated formulations, may be used to increase the amount of crystal protein applied per unit area, thereby enhancing the performance of the bioinsecticide product.

Previous efforts to create mutants or variants of *B.t.* strains that show enhanced production of crystal proteins have related primarily to the production of coleopteran- or dipteran-toxic crystal proteins, not CryI lepidopteran-toxic crystal proteins. Also, most of these examples describe oligosporogenous or asporogenous (produce few, if any, spores) variants of *B.t.* that show increased crystal protein production. As noted above, the full production of spores is a desirable feature for a lepidopteran-active *B.t.* strain used for the production of a commercial bioinsecticide.

U.S. Pat. No. 5,006,336, issued to Payne, describes a native *B.t.* isolate (PS122D3), active against coleopteran insects, which produces more coleopteran-toxic protein (CryIIIA) than an unrelated coleopteran-toxic *B.t.* strain, *B.t.* san diego. Strain PS122D3 is not a variant of *B.t.* strain san diego.

U.S. Pat. No. 4,996,156, issued to Zaehner et al., describes a dipteran-active *B.t.* israelensis mutant strain which produces crystal proteins but is asporogenous.

European Patent Application Publication No. O 099 30 of Fitz-James, describes mutants of *B.t. israelensis*, obtained using a chemical mutagen, that produces up to 1.5 times the amount of dipteran-toxic crystal protein as does the progenitor strain.

European Patent Application Publication No. O 228 228 of Mycogen Corporation, describes asporogenous *Bacillus thuringiensis* mutants obtained by treatment of the progenitor strains with ethidium bromide. Such *B.t.* mutants are described as being more efficient at producing coleopteran-toxic coleopteran-toxic crystal protein (CryIIIA) crystal protein.

PCT International Patent Application Publication No. WO 94/28724 of Ecogen, Inc. discloses a naturally occurring asporogenous *Bacillus thuringiensis* mutant that exhibits elevated levels of CryIIIA crystal protein.

PCT International Patent Application Publication No. WO 91/07481 of Novo Nordisk A/S, describes a mutant of *Bacillus thuringiensis* tenebrionis, which was obtained by gamma irradiation and which produces 2 times the amount of coleopteran-toxic crystal protein (CryIIIA) obtained from the progenitor strain.

U.S. Pat. No. 4,990,332, issued to Payne et al., describes a lepidopteran-toxic *B.t.* kurstaki mutant strain (PS85a1-168) that produces crystal protein in amounts "equal to or higher than the wild type" but is asporogenous.

The present invention relates to a naturally-occurring variant of *B.t.* strain kurstaki EG4923 that is more efficient in the production of CryI lepidopteran-toxic crystal protein than the progenitor strain EG4923. The variant strain, designated EG4923-4, also exhibits efficient sporulation comparable to that of the progenitor strain, making it ideal for use as a cost-effective lepidopteran-toxic bioinsecticide, particularly against insect pests such as *Spodoptera exigua*.

SUMMARY OF THE INVENTION

The subject invention concerns novel *Bacillus thuringiensis* isolates which have activity against all lepidopteran pests tested. This invention also concerns certain toxin crystal proteins produced by the *B.t.* strains, which proteins are toxic to lepidopteran insects. The toxin crystal proteins are the active ingredient in insecticidal compositions which are also the subject of the present invention. The genes encoding these toxin proteins can be transferred to the novel *Bacillus thuringiensis* strain of this invention via plasmid vectors.

Specifically, the invention comprises the novel *B.t.* isolate designated EG4923-4, derivatives thereof, and toxin crystal proteins derived from these *B.t.* isolates which are active against lepidopteran pests.

The *Bacillus thuringiensis* strains of this invention include a biologically pure culture of *Bacillus thuringiensis* bacteria deposited with the Agricultural Research Service Culture Collection, Northern Regional Research Laboratory (NRRL), having accession number NRRL B-21577 and being designated as EG4923-4. Also included are derivative strains capable of overproducing CryI lepidopteran-toxic crystal proteins. *B.t.* strain EG4923-4 sporulates efficiently and produces more CryI lepidopteran- toxic crystal protein than does progenitor strain EG4923.

The *Bacillus thuringiensis* strains of this invention also include recombinant derivatives of strain EG4923-4: derivatives that have been transformed with a recombinant plasmid containing an insecticidal crystal protein gene and capable of overproducing CryI lepidopteran-toxic crystal protein. These include biologically pure cultures of *Bacillus thuringiensis* bacteria, deposited with the NRRL, having the accession numbers NRRL B-21506, NRRL B-21507, NRRL B-21578 and designated strains EG11621, EG11622, and EG7841-1, respectively.

The *Bacillus thuringiensis* strains of this invention also include derivatives of strain EG4923-4 that contain a native plasmid containing an insecticidal crystal protein gene, transferred from a donor strain to strain EG4923-4 by a conjugation-like process or by phage transduction, and are capable of overproducing CryI lepidopteran-toxic crystal protein.

The invention also concerns insecticide compositions comprising the *B.t.* strains of this invention, insecticidal proteins produced by such *B.t.* strains and an agriculturally acceptable carrier, and to the methods of using such insecticidal compositions for insect control on plants.

DETAILED DESCRIPTION OF THE INVENTION

Figure 1:
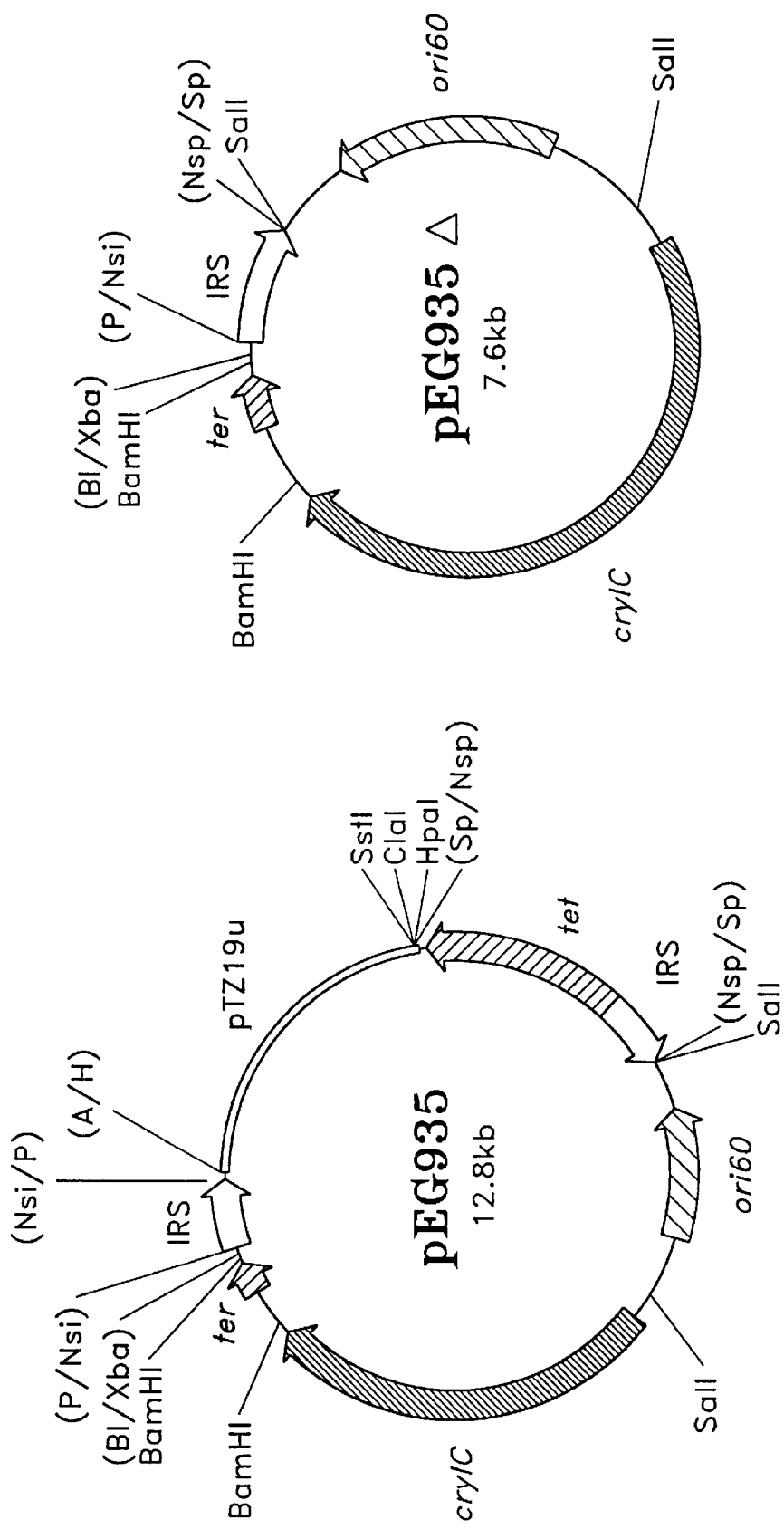
FIG. 1 comprises a structural map of the recombinant plasmid pEG935, containing the crylC insecticidal crystal protein gene, and the derivative of pEG935, designated pEG935Δ, present in strain EG11621. The boxed arrows indicate genes or functional DNA elements. Designations: pTZ19u=*E. coli* phagemid vector pTZ19u, tet=tetracycline resistance gene, ori60=*B. thuringiensis* plasmid replication origin, crylc=insecticidal crystal protein gene, ter=cryIF transcription terminator region, IRS=DNA fragment containing the internal resolution site region of transposon Tn5401. Restriction endonuclease abbreviations: A=Asp718, Bl=BlnI, H=HindIII, Nsi=NsiI, Nsp=NspI, P=PstI, Sp=SphI, Xba=XbaI.

A preferred novel *B. thuringiensis* isolate of the subject invention is designated EG4923-4. This isolate produces lepidopteran-toxic crystal proteins and is active against lepidopterans. The lepidopteran-toxic crystal proteins produced by EG4923-4 include CryIAc and CryIIA. Derivatives of the *B. thuringiensis* isolate EG4923-4 harboring recombinant plasmids containing at least one crystal protein nucleotide sequence, are designated EG11621, EG11622, and EG7841-1. These derivatives are capable of increased production of other lepidopteran-toxic crystal proteins in addition to CryIAc crystal protein. The four strains are capable of increased production of certain lepidopteran-toxic crystal proteins, preferably in the size range of about 125 to about 140 kilodaltons, including and not limited to CryIA and CryIC.

*B. thuringiensis* EG4923-4, EG11621, EG11622, and EG7841-1 may be cultured using standard known media and fermentation techniques. Upon completion of the fermentation cycle, the bacteria can be harvested by separating the *B.t.* spores and crystals from the fermentation broth by means well known in the art, such as and not limited to centrifugation. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. The *B.t.* isolates of the present invention can be used to control lepidopteran pests.

A subculture of *B.t.* EG4923-4, EG11621, EG11622, and EG7841-1, were prepared in accordance with the methods set forth in the Examples and were deposited in the permanent collection of the Agricultural Research Service Culture Collection, Peoria, Ill. on Jun. 25, 1996. The accession numbers are as follows:

| Bacterial strain | NRRL Accession Number | Date of Deposit |
| --- | --- | --- |
| EG4923-4 | NRRL B-21577 | May 21, 1996 |
| EG11621 | NRRL B-21506 | November 15, 1995 |
| EG11622 | NRRL B-21507 | November 15, 1995 |
| EG7841-1 | NRRL B-21578 | May 21, 1996 |

The subject cultures have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Methods of screening for *B.t.* strains showing improved production of certain lepidopteran-toxic crystal proteins comprise inoculating a culture medium with about 100 to about 500 colony forming units of *Bacillus thuringiensis*, preferably B.t. strain EG4923. The culture medium may be solid such as and not limited to starch agar plates or nutrient broth salt agar plates. The culture may be grown for about one to about fourteen days, preferably about three days, even more preferably about five days, and even more preferably about seven days, at a temperature of about 25° C. to about 37° C., preferably about 30° C. Certain colonies were observed to be white and crusty in appearance and opaque as compared to usual EG4923 colonies which are creamy white and shiny. One such colony was examined for crystal protein production and was found to be increased as compared to progenitor strain EG4923.

Derivatives of the *Bacillus thuringiensis* isolate EG4923-4 may be prepared by recombinant methods including and not limited to recombinant plasmids containing an insecticidal crystal protein gene and by phage transduction or by a conjugation-like process. The derivatives EG11621, EG11622, and EG7841-1 have been transformed with a recombinant plasmid containing an insecticidal crystal protein gene and are capable of overproducing CryI lepidopteran-toxic crystal protein. In addition, derivatives of Bt strain EG4923-4 contain a native plasmid containing an insecticidal crystal protein gene transferred from a donor strain to strain EG4923-4 by a conjugation-like process or by phage transduction and are capable of overproducing CryI lepidopteran-toxic crystal protein.

A wide variety of ways are available for introducing a *B.t.* gene expressing a toxin into the *B. thuringiensis* host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host.

A number of transcriptional regulatory regions are available from *Bacillus thuringiensis*. Various transcriptional regulatory regions include the regions associated with the α amylase gene, phospholipase C gene, exoproteinase gene, and the naturally-occurring promoters associated with the toxin gene or other Cry toxin genes, where functional in the host. See for example, Chak et al., *Appl. Environ. Microbiol.*, 1994, 60:2304–2310, PCT W094/25611 of Sandoz Ltd., and PCT W092/14826 of Ciba Geigy. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pEG147, pHT3101, pEG597, pEG853, pEG854, pHV33, and the like. See for review, Gawron-Burke, C., and Baum, J. A., *Genetic Engineering* 1991, 13:237–263.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity. When desired, unwanted or ancillary DNA sequences may be selectively removed from the recombinant bacterium by employing a site specific recombination system as described in U.S. Pat. No. 5,441,884.

The B.t. cells containing a *B.t.* crystal protein gene may be grown in any convenient nutrient medium that allows for efficient sporulation, where the DNA construct provides a selective advantage, providing for a selective medium so that substantially all or all of the cells retain the *B.t.* gene. Following fermentation, the spores and crystals may then be harvested in accordance with conventional methods.

The *B.t.* spores and crystals may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

The insecticidal concentration will vary widely depending upon the nature of the particular formulation, particularly whether it is a concentrate or to be used directly. The insecticide will be present in at least 1% by weight and may be 100% by weight. The dry formulations will have from about 1% to about 95% by weight of the pesticide while the liquid formulations will generally be from about 1% to about 75% by weight of the solids in the liquid phase. The formulations will be administered at about 1 gram (liquid or dry) to about 1 kg or more per hectare.

The formulations can be applied to the environment of the lepidopteran pest(s), e.g., plants, soil or water, by spraying, dusting, sprinkling, or the like. Applications will be set with regard to conditions specific to the pest and environment such as and not limited to crop, weather conditions, insect pressure and population. The proportional ratio of active ingredient to carrier will naturally depend on the chemical nature, solubility, and stability of the insecticidal composition, as well as the dosage contemplated.

The insecticidal compositions of the invention may be employed in the methods of the invention singly or in combination with other compounds, including and not limited to other pesticides, such as and not limited to insect pheremones. The method of the invention may also be used in conjunction with other treatments. The insecticidal composition of the present invention may be administered by any suitable route, including and not limited to topical sprays.

To prepare phage resistant variants of *B.t.*, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

The present invention is further described in the following examples. These examples are not to be construed as limiting the scope of the appended claims.

EXAMPLE 1

Isolation of EG4923 Variants

Strain EG4923 subspecies kurstaki is a transconjugant derivative of strain EG3125, a native B.t. strain obtained from a New York grain dust sample. Strain EG4923 contains three cryIAc genes encoding lepidopteran-toxic CryIAc crystal proteins and one cryIIA gene encoding a lepidopteran- and dipteran- toxic CryIIA crystal protein. Two copies of the cryIAc gene and the one copy of the cryIIA gene are present on a plasmid of approximately 110 megadaltons in mass. The remaining cryIAc gene is contained on a self-transmissible plasmid of approximately 56 megadaltons.

Strain EG4923 was grown at 30° C. in DSM broth culture medium, described by Donovan et al., *Appl. Environ. Microbiol.* 1992, 58:3921–3927, for three days, at which time sporulation and cell lysis had occurred. The culture was diluted 1/10,000 with water and 40 microliters of the diluent plated onto starch agar (DIFCO) plates supplemented with 5g/liter agar. The plates were incubated at 30° C. overnight. The following day, the plates were examined for colonies displaying an unusual morphology. EG4923 colonies typically exhibit a creamy-white shiny appearance. Four colony morphology variants were isolated from the plates, streaked onto fresh starch agar plates, and designated EG4923-1, EG4923-2, EG4923-3, and EG4923-4. Isolates 1 and 2 appeared less opaque than the typical EG4923 colony while isolates 3 and 4 appeared whiter and crusty in texture when compared to the typical EG4923 colony. Further examination of the isolates by phase contrast microscopy suggested that isolates 1 and 2 were delayed in sporulation whereas isolates 3 and 4 exhibited apparently normal sporulation. All four isolates produced bipyramidal shaped crystals typical of lepidopteran-toxic CryI crystal proteins.

Figure 4:
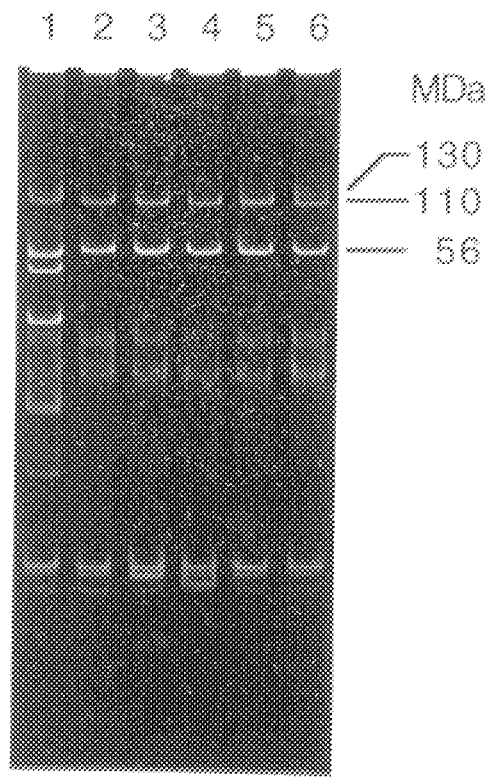
FIG. 4 is a photograph of an agarose gel demonstrating that isolate EG4923-4 was missing a 130 megadalton plasmid. Lanes 1 =HD1, 2 =EG11622, 3 =EG7841-1 (EG11730), 4 =EG7841-4 (EG11621), 5 =EG4923-4, and 6 =EG4923.

The array of plasmids contained in the four EG4923 variants was determined by agarose gel electrophoresis using a modified Eckhardt agarose gel electrophoresis procedure described by Gonzalez Jr. et al., *Proc. Natl. Acad. Sci USA* 1982, 79:6951–6955. This analysis demonstrated that isolates 1, 2, and 4 contained the crystal protein-encoding plasmids of strain EG4923. In contrast, isolate 3 was determined to be a contaminant strain unrelated to strain EG4923. In addition, isolate 4, designated EG4923-4, was found to be missing a 130 megadalton plasmid which plasmid appears to not contain a toxin gene, see FIG. 4. While not intending to be bound by any particular theory of operation, it is believed that the B.t. strains of the present invention may produce increased amounts of CryI crystal proteins due to the lack of the 130 megadalton plasmid.

EXAMPLE 2

Crystal Protein Production by EG4923 Variants

Strain EG4923 and the variants EG4923-1, EG4923-2, and EG4923-4 were inoculated into 25 ml flasks containing 8 ml of broth culture consisting of 14.4 g/l soyflour, 7.9 g/l meat peptone, 20.0 g/l cerelose, 3.1 g/l anhydrous $KH_2PO_4$, 4.7 g/l $K_2HPO_4$, 1×C2 salts (described by Donovan et al., *J. Biol Chem.* 1988, 263:561–567), titrated to pH 7.5 with 1N NaOH.

The cultures were grown in duplicate for three days at 25° C. After three days, at which time sporulation and cell lysis had occurred, crystal protein production was quantitated by the SDS-polyacrylamide gel (PAGE) method described by Brussock, S. M., and Currier, T. C., 1990, "Use of Sodium Dodecyl Sulfate-Polyacrylamide Gel Electrophoresis To Quantify *Bacillus thuringiensis* δ-Endotoxins", in *Analytical Chemistry of Bacillus thuringiensis.* (L. A. Hickle and W. L. Fitch, eds.), The American Chemical Society, pp. 78–87. The procedure was modified to eliminate the neutralization step with 3M HEPES. Crystal proteins resolved by SDS-PAGE were quantitated by densitometry using a Molecular Dynamics model 300A computing densitometer and purified CryIAc crystal protein as a standard. The results shown in Table 1 demonstrate that variant EG4923-4 produced 30% more CryIAc crystal protein than did the progenitor strain EG4923. Variants EG4923-1 and EG4923-2 produced less crystal protein than did the progenitor strain EG4923.

TABLE 1

Crystal protein overproduction by variant EG4923-4

| Strain | | Relative crystal protein yield[1] |
|---|---|---|
| EG4923-1 | culture #1 | 0.70 |
| EG4923-1 | culture #2 | 0.73 |
| EG4923-2 | culture #1 | 0.86 |
| EG4923-2 | culture #2 | 0.81 |
| EG4923-4 | culture #1 | 1.32 |
| EG4923-4 | culture #2 | 1.31 |

[1]Crystal protein yield relative to the yield of strain EG4923, defined as 1.0.

EXAMPLE 3

Figure 2:
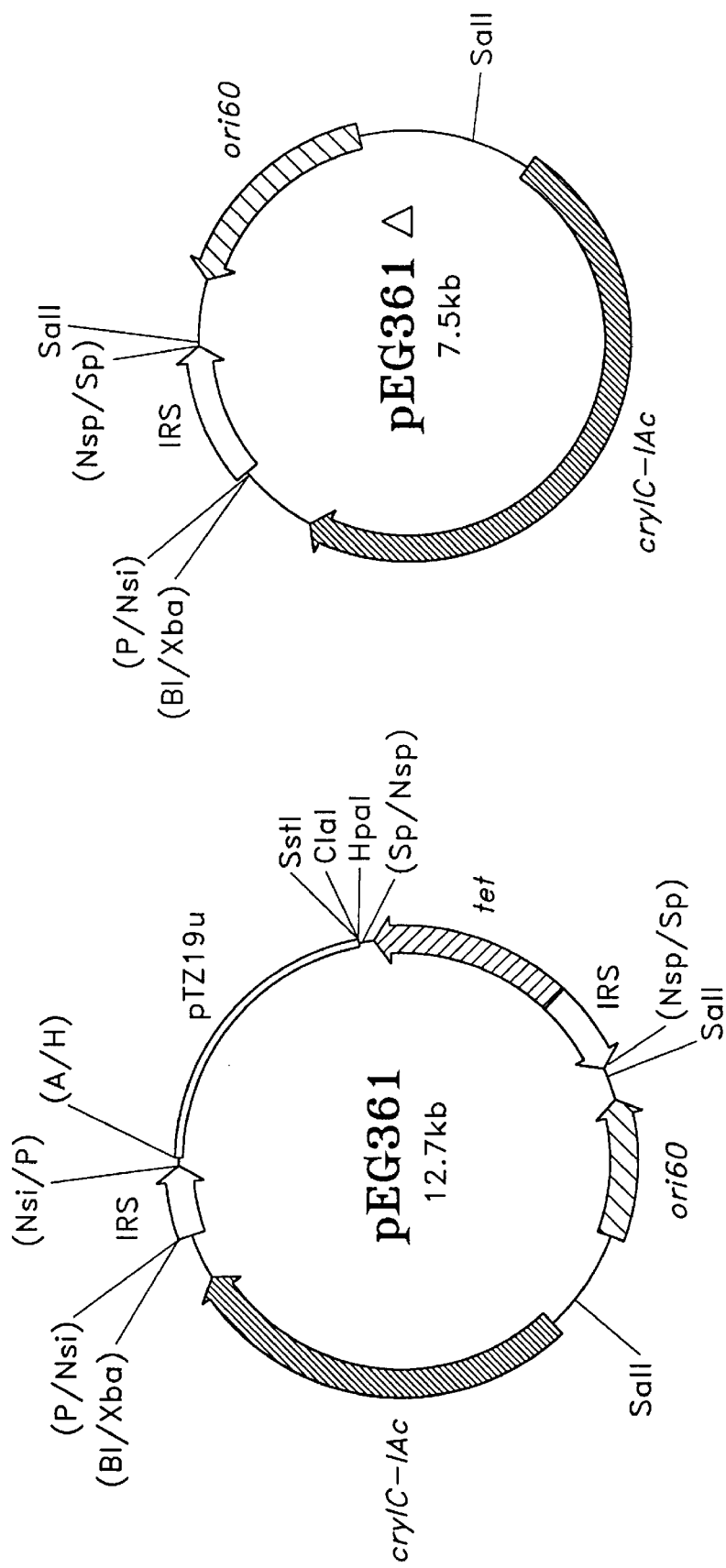
FIG. 2 comprises a structural map of the recombinant plasmid pEG361, containing the cryIC-IAc insecticidal crystal protein gene, and the derivative of pEG361, designated pEG361Δ, present in strain EG11622. Boxed arrows indicate genes or functional DNA elements. Designations: pTZ19u=*E. coli* phagemid vector pTZ19u, tet=tetracycline resistance gene, ori60=*B. thuringiensis* plasmid replication origin, cryIC-IAc=insecticidal crystal protein gene, IRS=DNA fragment containing the internal resolution site region of transposon Tn5401. Restriction endonuclease abbreviations: A=Asp718, Bl=BlnI, H=HindIII, Nsi=NsiI, Nsp=NspI, P=PstI, Sp=SphI, Xba=XbaI.

Construction of EG4923-4 Recombinant Derivatives Capable of Overproducing CryI Lepidopteran-Toxic Crystal Protein Strain EG4923-4 may be used as a host strain for producing, at high levels, lepidopteran-toxic crystal proteins in addition to the CryIAc crystal protein. To demonstrate this, recombinant plasmids containing the cryIC and cryIC-IAc crystal protein genes were introduced into strain EG4923-4 using the electroporation procedure described by Mettus, A. M. and A. Macaluso, *Appl. Environ. Microbiol.* 1990, 56:1128–1134. The recombinant plasmids containing cryIC and cryIC-IAc are designated pEG935 (FIG. 1) and pEG361 (FIG. 2), respectively, and are similar in structure to the cryI plasmids described in U. S. Pat. No. 5,441,884.

Strain EG4923-4 transformants containing plasmids pEG935 and pEG361 were isolated on Luria plates containing 10 μg/ml tetracycline. Recombinant plasmid DNAs from the transformants were isolated by the alkaline lysis procedure described by Baum, J. A., *J. Bacteriol.* 1995, 177:4036–4042 and confirmed by restriction enzyme analysis performed according to standard methods such as those set forth in Maniatis et al., 1982 *Molecular Cloning: A Laboratory Manual*, Cold Spring Harbor Laboratory, Cold Spring Harbor. The plasmid arrays of the transformants were further confirmed by the Eckhardt agarose gel analysis procedure described by Gonzalez Jr. et al., *Proc. Natl. Acad. Sci USA* 1982, 79:6951–6955. The EG4923-4 recombinant derivatives were designated EG4923-4/pEG935 and EG4923-4/pEG361. For comparison, plasmid pEG935 was introduced into the progenitor host strain EG4923 by electroporation to yield strain EG4923/pEG935.

Crystal protein yields obtained with strains EG4923-4/pEG935 and EG4923-4/pEG361 were determined as described previously and compared to that obtained with EG4923/pEG935. As shown in Table 2, both recombinant strains retain the ability to overproduce lepidopteran-toxic crystal protein when compared to the progenitor strain EG4923 harboring plasmid pEG935.

TABLE 2

Crystal protein overproduction by EG4923-4 recombinant derivatives.

| Strain | Relative crystal protein yield[1] |
|---|---|
| EG4923-4/pEG935 | 1.32 |
| EG4923-4/pEG361 | 1.19 |

[1]Crystal protein yield relative to the yield of strain EG4923/pEG935, defined as 1.0.

EXAMPLE 4

Figure 3:
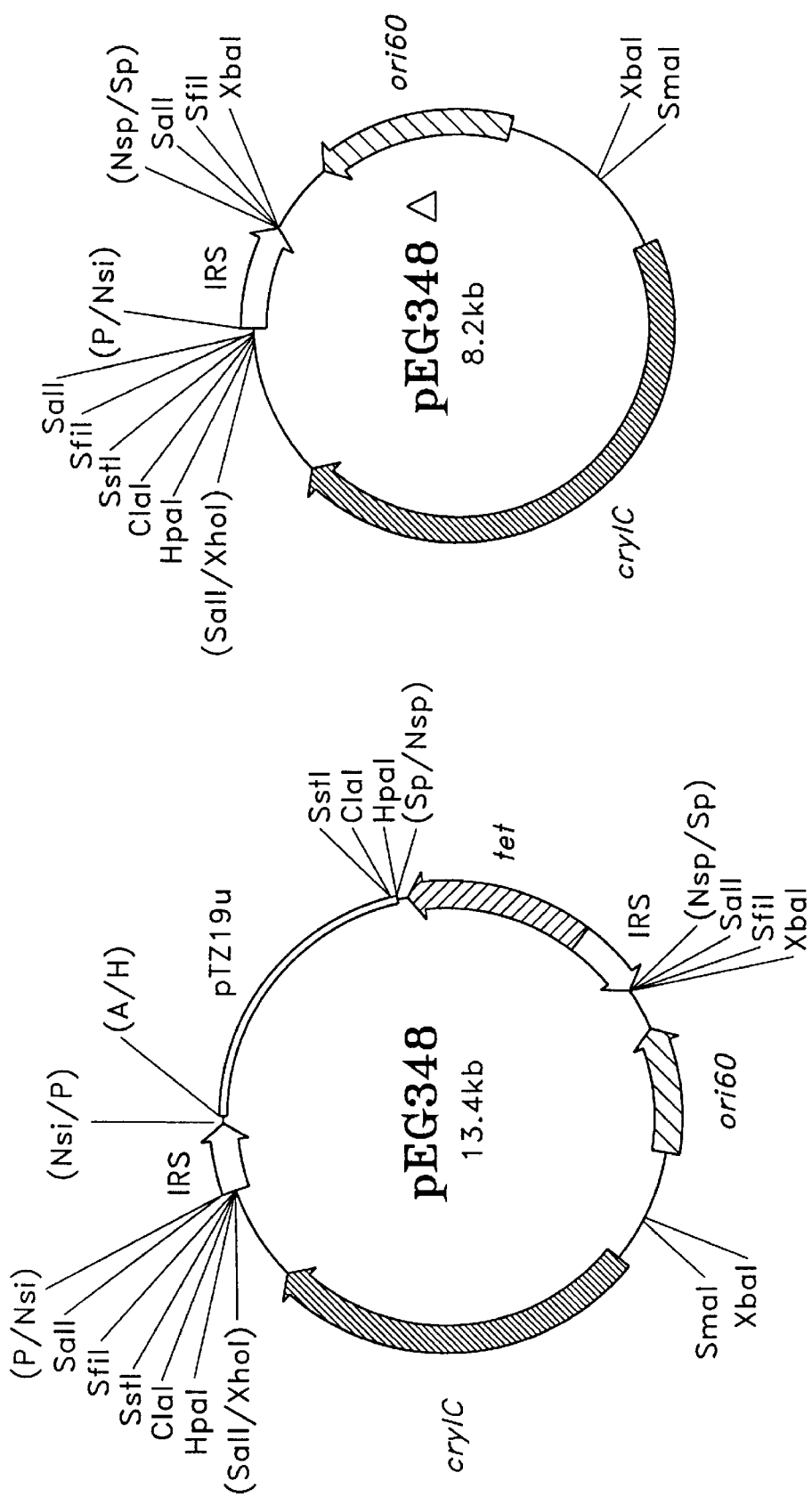
FIG. 3 comprises a structural map of the recombinant plasmid pEG348, containing the crylc insecticidal crystal protein gene, and the derivative of pEG348, designated pEG348Δ, present in strain EG7841-1. The boxed arrows indicate genes or function DNA elements. Designations: pTZ19u=*E. coli* phagemid vector pTZ19u, tet=tetracycline resistance gene, ori60=*B. thuringiensis* plasmid replication origin, crylc=insecticidal crystal protein gene, IRS=DNA fragment containing the internal resolution site region of transposon Tn5401. Restriction endonuclease abbreviations: A=Asp718, H=HindIII, Nsi=NsiI, Nsp=NspI, P=PstI, Sp=SphI.

Modification of Strains EG4923-4/pEG935, EG4923-4/pEG361, and EG4923-4/pEG348 to Remove Foreign DNA Elements Plasmids pEG935 (FIG. 1), pEG361 (FIG. 2), and pEG348 (FIG. 3) contain duplicate copies of a site-specific recombination site or internal resolution site (IRS) that serves as a substrate for an in vivo site-specific recombination reaction mediated by the TnpI recombinase of transposon Tn5401 (described in Baum, J. A., *J. Bacteriol.* 1995, 177:4036–4042). This site-specific recombination reaction, described in U.S. Pat. No. 5,441,884, results in the deletion of non-*B.t.* DNA or foreign DNA elements from the crystal protein-encoding recombinant plasmids. The resulting recombinant *Bacillus thuringiensis* strains are free of foreign DNA elements, a desirable feature for genetically engineered strains destined for use as bioinsecticides for spray-on application. Strains EG4923-4/pEG935, EG4923-4/pEG361, and EG4923-4/pEG348 were modified using this in vivo site-specific recombination (SSR) system to generate three new strains, designated EG11621, EG11622, and EG7841-1, respectively (Table 3).

TABLE 3

Recombinant derivatives of strain EG4923-4

| Strain | Alias | Recombinant plasmid | Progenitor strain |
|---|---|---|---|
| EG11621 | EG4923-4/pEG935Δ | pEG935Δ | EG4923-4/pEG935 |
| EG11622 | EG4923-4/pEG361Δ | pEG361Δ | EG4923-4/pEG361 |
| EG7841-1 | EG4923-4/pEG348Δ | pEG348Δ | EG4923-4/pEG348 |

These strains, designated EG11621, EG11622, and EG7841-1, retain the ability to overproduce CryI lepidopteran-toxic crystal proteins. As an example, the crystal protein yield obtained with strain EG7841-1 (alias EG4923-4/pEG348Δ) is compared to that obtained with strain EG4923/pEG348Δ in Table 4 using the same methods described in Example 2. These results show an approximately 40% increase in the yield of CryI lepidopteran-toxic protein.

TABLE 4

Crystal protein overproduction by strain EG7841-1

| Strain | Relative crystal protein yield[1] |
|---|---|
| EG4923/pEG348Δ | 1.0 |
| EG7841-1 | 1.4 |

[1]Crystal protein yield relative to the yield of strain EG4923/pEG348Δ, defined as 1.0.

All three strains listed in Table 3 produce a CryIC toxin protein, a toxin known to be effective against the beet armyworm Spodoptera exigua, in addition to CryIAc toxin protein. These strains can be used in bioinsecticide compositions to control many lepidopteran insect pests, particularly *Plutella xylostella, Trichoplusia ni,* and *Spodoptera exigua*. The efficient production of spores by these strains further contributes to their toxicity, particularly towards *S. exigua*.

The disclosures of each patent, patent application, and publication cited or described herein are hereby incorporated herein by reference in their entirety.

Various modifications of the invention in addition to those shown and described herein will be apparent to those skilled in the art from the foregoing description. Such modifications are also intended to fall within the scope of the appended claims.

What is claimed:

1. *Bacillus thuringiensis* kurstaki strain EG4923-4 having the NRRL accession number B-21577, which has been transformed with a heterologous δ-endotoxin gene.

2. *Bacillus thuringiensis l kurstaki strain EG*4923-4 having the NRRL accession number B-21577.

3. *Bacillus thuringiensis* kurstaki strain EG11621 having the NRRL accession number B-21506.

4. *Bacillus thuringiensis* kurstaki strain EG11622 having the NRRL accession number B-21507.

5. *Bacillus thuringiensis* kurstaki strain EG7841-1 having the NRRL accession number B-21578.

6. An insecticidal composition comprising an insecticidally effective amount of a lepidopteran toxic crystal protein and spores obtained from the *Bacillus thuringiensis* strain of claim 1, 2, 3, 4 or 5, and a suitable carrier.

* * * * *